United States Patent [19]

Henry et al.

[11] Patent Number: 5,339,820
[45] Date of Patent: Aug. 23, 1994

[54] IMPLANTABLE CARDIAC MONITORING AND/OR CONTROL DEVICES HAVING AUTOMATIC SENSITIVITY CONTROL, APPARATUS AND METHODS THEREFOR

[75] Inventors: Christine Henry, Paris; Remy Nitzsche, Gambais, both of France

[73] Assignee: ELA Medical, Montrouge, France

[21] Appl. No.: 994,725

[22] Filed: Dec. 22, 1992

[30] Foreign Application Priority Data

Dec. 23, 1991 [FR] France ............... 91 15980

[51] Int. Cl.$^5$ .............................................. A61B 5/04
[52] U.S. Cl. .................................................. 128/696
[58] Field of Search ............... 128/419 PG, 696, 708, 128/901, 902; 607/9

[56] References Cited

U.S. PATENT DOCUMENTS

| | | | |
|---|---|---|---|
| 3,927,677 | 12/1975 | Gobeu et al. | 128/419 PG |
| 3,939,824 | 2/1976 | Arngson et al. | 128/708 |
| 3,986,496 | 10/1976 | Brastad | 128/2.06 R |
| 4,226,245 | 10/1980 | Bennett, Jr. | 128/419 PT |
| 4,250,883 | 2/1981 | Thompson | 128/419 PG |
| 4,325,384 | 4/1982 | Blaser et al. | 128/419 PG |
| 4,617,938 | 10/1986 | Shimoni et al. | 128/708 |
| 4,766,902 | 8/1988 | Schroeppel | 128/419 PG |
| 4,768,511 | 9/1988 | Decote, Jr. | 128/419 PG |
| 5,010,887 | 4/1991 | Thornander | 128/708 |
| 5,117,824 | 6/1992 | Keimel et al. | 129/419 D |

FOREIGN PATENT DOCUMENTS 0321764 6/1989 European Pat. Off. ........ A61N 1/37

*Primary Examiner*—William E. Kamm
*Attorney, Agent, or Firm*—Davis Hoxie Faithfull & Hapgood

[57] ABSTRACT

A method for automatic control of sensitivity, for implanted pacemaker, cardioversion and/or cardiac defibrillation device. Prior to the start of the cardiac cycle, the sensitivity threshold is set to a low value (Smax) so as to have maximum sensitivity. Upon detection of a ventricular complex, the amplitude is measured and the sensitivity threshold S is set to the value of that amplitude. The sensitivity threshold subsequently decreases in stages to return to the low value Smax.

32 Claims, 3 Drawing Sheets

IMPLANTABLE CARDIAC MONITORING AND/OR CONTROL DEVICES HAVING AUTOMATIC SENSITIVITY CONTROL, APPARATUS AND METHODS THEREFOR

BACKGROUND OF THE INVENTION

This invention relates to a method for automatic control of sensitivity for an implanted cardiac control device, such as a pacemaker, cardioversion and/or cardiac defibrillation device, and to corresponding devices having enhanced sensitivity control.

In cardiac control devices, such as pacemakers and defibrillators, the pertinent electrical signals have amplitudes spread over a range extending, e.g., from a few tenths of a millivolt (e.g., the amplitude of the P wave is in the region of 0.4 mV) to a few millivolts (e.g., the amplitude of the R wave is often between 5 and 10 mV). To ensure satisfactory operation whatever the amplitude of the signal received, some of these cardiac control devices are fitted with an automatic gain control.

French patent No. 2,606,644 describes an implantable device having a pacing and cardioversion function, using an automatic gain control in the amplitude circuit of weak cardiac signals, such as those of ventricular fibrillation.

European patent No. 340,045 describes a cardioversion device using three sensitivities: the first being an average sensitivity for detection of the sinus rhythm and ventricular tachycardia, the second being a higher sensitivity for differentiating ventricular fibrillation and asystole, and the third being a lower sensitivity for differentiating the R wave and the lesional T wave at high amplitude. However, one of these three sensitivities is selected as a function of the status of the device (period of suspected tachycardia, or postshock period), and is maintained at least until the next cycle.

There are two types of drawbacks in the case of sensitivity that can be switched between three values. The first is that of oversensing when the sensitivity is too high: T waves can then be detected and mistaken for R waves upon which the pacemaker recycles itself. This can lead the rhythm analysis system to err (e.g., the rhythm is found to be faster than it actually is). The second is that of undersensing when the sensitivity is too low. In this case, R waves can fail to be detected and the operating of the device is no longer adapted to the patient's heart.

U.S. Pat. No. 5,117,824 refers to a cardiac pacemaker and/or cardioverter/defibrillator that has an R-wave detector and adjusts its sensing threshold in response to R-wave amplitude. The detection threshold is selected as a predetermined proportion of the amplitude of a detected R-wave. The threshold then decays over a period of less than three seconds to a fixed, lower threshold value. Redefinition of the threshold is prevented for a predetermined time period following delivery of a pacing pulse to return the threshold to its lowest value during pacing.

SUMMARY OF THE INVENTION

It is, therefore, an object of the present invention to remedy the aforementioned disadvantages and to provide for automatic control of sensitivity for a cardiac control device, such as a pacemaker, cardioversion and/or cardiac defibrillation device and to provide such a device having improved automatic sensitivity control for monitoring the desired electrical signals.

A further object of the invention is the application of the automatic control of sensitivity to a heart pacing device, or to a cardioversion and/or cardiac defibrillation device.

Another object of the invention is to provide a cardiac pacing, cardioversion and/or cardiac defibrillation device characterized in that it comprises a sensitivity threshold that can be adjusted automatically for improved signal detection.

Broadly, the invention concerns automatic control of electric signal sensitivity by ensuring a variation of the sensitivity during the cardiac cycle, thereby avoiding oversensing and undersensing. One aspect of the invention concerns a method for automatic control that is characterized by:

(a) initially setting a sensitivity threshold to a low value (Smax), so as to have maximum sensitivity;

(b) upon detection of a ventricular complex, the amplitude (Amp) of the ventricular complex is measured and the sensitivity threshold (S) is re-computed as a function of that amplitude (Amp); and (c) the sensitivity threshold subsequently decreases in stages, so as to tend towards the low value (Smax). Preferably, the decreasing in stages of the sensitivity threshold takes place by decrements (DecS), which may be fixed increment or percentage reductions.

A maximum period (Tmax) is provided, which is counted from the detection of the ventricular complex. At the end of the maximum period Tmax, the sensitivity threshold is automatically returned to the low value (Smax) corresponding to maximum sensitivity. This is to sense low amplitude cardiac events.

The amplitude (Amp) of the ventricular complex is measured during a time window, selected from between 16 and 110 ms, preferably 64 ms. The time window is counted from detection of a ventricular complex. Preferably, the amplitude (Amp) is the maximum amplitude, more preferably, the maximum of the rectified ventricular complex signal.

The aforementioned method for automatic control of sensitivity may be implemented in a cardiac control device, particularly in conventional cardiac pacemakers, cardioversion devices and/or cardiac defibrillators. The result is an improved device having a controllably variable sensitivity threshold that provides enhanced signal detection for use in performing their customary cardiac monitoring and related functions. Hence, in accordance with the present invention, the improved cardiac control devices function in their respectively known manners, except that their sensitivity thresholds are now variable as described herein. The result is an improved device that is less susceptible to improperly responding to cardiac electrical signals.

BRIEF DESCRIPTION OF THE DRAWINGS

Further features and advantages of the invention will be apparent upon consideration of the following detailed description of a preferred embodiment of the present invention, taken in conjunction with the accompanying drawings, in which.

DETAILED DESCRIPTION OF THE INVENTION

Figure 1:
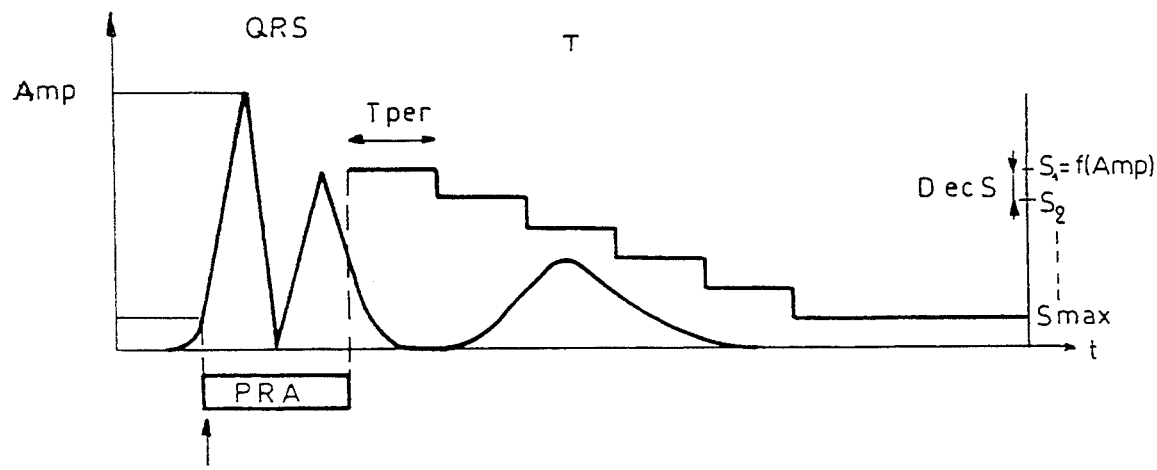
FIG. 1 is a simplified diagram of a sample typical filtered and rectified ventricular cardiac signal, with a representation of the variable sensitivity threshold stages of an embodiment of the invention.
Figure 2:
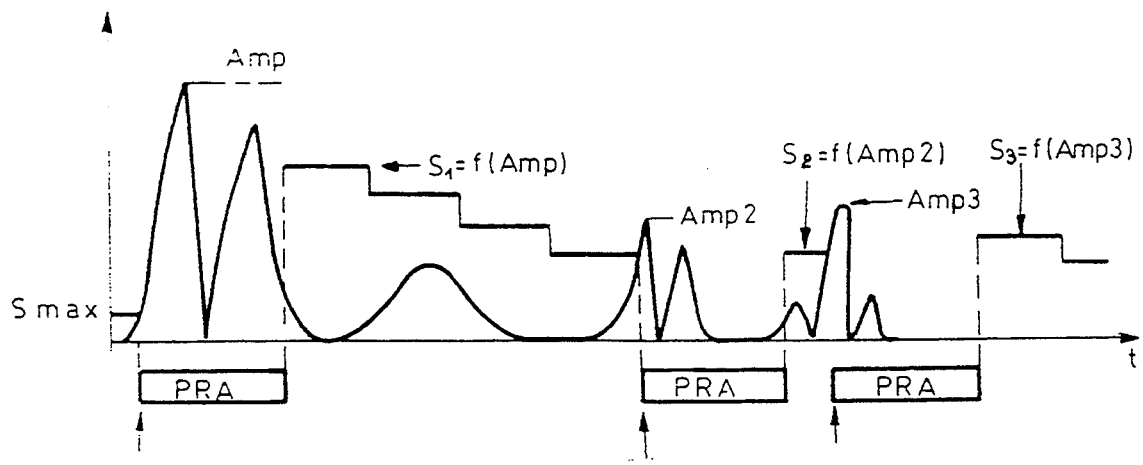
FIG. 2 is another simplified diagram of a sample cardiac signal corresponding to the occurrence of a ventricular complex, with representation of the variable sensitivity threshold stages in accordance with an embodiment of the invention.

In FIGS. 1 and 2, the time t is graphed along the X-axis and the amplitude A of the rectified sensed cardiac signals is graphed along the Y-axis.

Referring to FIG. 1, the R and T waves of a classical cardiac ventricular signal are illustrated. Also represented are the maximum sensitivity threshold Smax, the decrease (or decrement) step DecS of the sensitivity threshold (the vertical axis on the right-hand side of the figure), and the staircase waveform corresponding to the controlled variations of the sensitivity threshold which occur during the cardiac cycle.

Referring to FIG. 2, the amplitude of the ventricular fibrillation signals illustrated on the right side of the plot are low with regard to the amplitude of the sinus rhythm signals illustrated on the left side of the plot (and in FIG. 1). A high sensitivity is therefore required to detect ventricular fibrillation, i.e., a low sensitivity threshold Smax. However, if the sensitivity is high and the threshold Smax low, then the T wave (shown in FIG. 1) is detected and risks being mistaken for an R wave (the case of oversensing).

To avoid a detection of the T wave, it is possible to provide a sufficiently long ventricular absolute refractory period (exceeding 300 ms). However, in a cardiac monitoring device whose function is to detect short coupling rhythms (R—R interval below 300 ms), this solution cannot be used.

According to the present invention, the sensitivity of the device during a cardiac cycle is responsive to the amplitude of the ventricular signal upon which the cycle started. A ventricular signal, i.e., a QRS complex, is detected if its amplitude exceeds the provided sensitivity threshold at the time of detection.

In the case of detection of an event, two periods begin. One period is a ventricular absolute refractory period PRA of, e.g., 110 ms. The other period is a window of, e.g., 16 to 110 ms, preferably 64 ms (not illustrated). During the duration of the window, the amplitude Amp of the rectified cardiac signal is measured, preferably the peak amplitude.

After the expiration of the window period, and during the absolute refractory period PRA, the sensitivity threshold to be applied at the end of the PRA is computed as value S1. The value S1 of the threshold is a function of the determined amplitude Amp, i.e., S1=Amp×75%. Of course, some other percent or function could be used, but a linear relation of 75% of the maximum rectified cardiac signal amplitude has been found to be suitable. It has been found to be effective in discriminating between T waves following a sensed R wave peak and a following R wave which may occur from, e.g., a premature ventricular contraction or a following cardiac cycle (sinus or fibrillation).

The calculated value S1 of the threshold is then made effective at the end of the absolute refractory period PRA, for a period Tper. At the end of the period Tper, the value S1 of the sensitivity threshold is decreased by a selected decrement DecS to a value S2. Accordingly, the sensitivity of the device increases, and the new value S2 of the sensitivity threshold is applied for a new period Tper. Preferably each period Tper has the same time interval.

The process continues to decrease periodically the sensitivity threshold S until either the value of the sensitivity threshold S(n), for n being the number of periods Tper, reaches the value Smax corresponding to maximum sensitivity, or a new ventricular detection occurs, which relaunches the process.

In this manner, in the case of a normal sinus rhythm (FIG. 1), the evolution of the sensitivity over the cardiac cycle is such that the T wave is not detected. In fact, the detection of the R wave entails a reduction of the sensitivity which masks the T wave related to that R wave. The sensitivity then increases step-by-step during the cycle, enabling the detection of subsequent events of low amplitude. Accordingly, the decrement DecS and period Tper are selected in some combination to achieve this result. One suitable combination has been found to be fixed amounts where Tper=47 ms and DecS=0.8 mV.

In FIG. 2, the left-hand side represents a sinus cardiac signal similar to that of FIG. 1, and the right-hand side represents the start of a cardiac disturbance such as fibrillation. The sensed amplitudes Amp2, Amp3 of the fibrillation signals are distinctly lower than that of a sinus signal amplitude Amp.

Working from the left-hand side of FIG. 2, the maximum sensitivity threshold Smax enables detection of the R wave, as well as triggering of the first ventricular absolute refractory period PRA and of the window for measuring the peak amplitude Amp of the rectified signal. At the end of the first absolute refractory period PRA, the value S1 of the sensitivity threshold is applied, which is calculated as a function of the measured amplitude:

$$S1 = f(Amp).$$

Subsequent to a first period of duration Tper, the value of the sensitivity threshold is reduced by a decrement DecS.

After a further period Tper, the value of the sensitivity threshold is decreased by a decrement DecS, and so on until a second cardiac signal is detected.

Detection of the second cardiac signal triggers a second absolute refractory period PRA and a corresponding window. During the second window, the amplitude AMP2 of the rectified second cardiac signal is measured. With regard to a fibrillation signal, its amplitude Amp2 is substantially lower than the amplitude Amp of the preceding sinus signal. At the end of the second absolute refractory period PRA, the new sensitivity threshold S2=f(Amp2) is applied.

During the first period Tper in which S2 is applied in the example represented, a new cardiac detection occurs. This triggers a new (third) absolute refractory period PRA and corresponding window, during which the amplitude Amp3 of the new (third) sensed cardiac signal is measured. At the end of the third absolute refractory period PRA, the sensitivity threshold S3=f(Amp3) is applied. At the end of a new first period Tper, the value S3 of the threshold is reduced by a decrement DecS, and so on until a new cardiac event is detected or the low value is reached.

In the method embodying the invention, the maximum sensitivity threshold Smax is always low, and the corresponding sensitivity is therefore always high, thereby enabling low-amplitude cardiac events to be detected. From the time of detection of an event, i.e., at the start of the cardiac cycle, the sensitivity threshold is computed as a function of the maximum amplitude of the cardiac signal detected, and the sensitivity is therefore decreased.

After the absolute refractory period PRA, the sensitivity threshold is decreased by decrements DecS and in stages of duration Tper, until it redescends to the maximum sensitivity threshold Smax, or until a new event is detected. The sensitivity thus becomes low after a detection, and increases in stages during the course of the cycle, tending towards its maximum value.

Advantageously, in accordance with the present invention, the oversensing phenomenon is avoided because the T wave has an amplitude below the sensitivity threshold at the moment corresponding to the T wave peak. The phenomena of undersensing also is avoided because the maximum sensitivity threshold is low with a view to detecting the low-amplitude R waves (e.g., in the case of fibrillation).

The following parameters also can be provided within the scope of the invention: a minimum sensitivity threshold Smin, and a maximum period Tmax counted from the time of detection, and at the end of which the sensitivity threshold imperatively descends to the value Smax.

Figure 3:
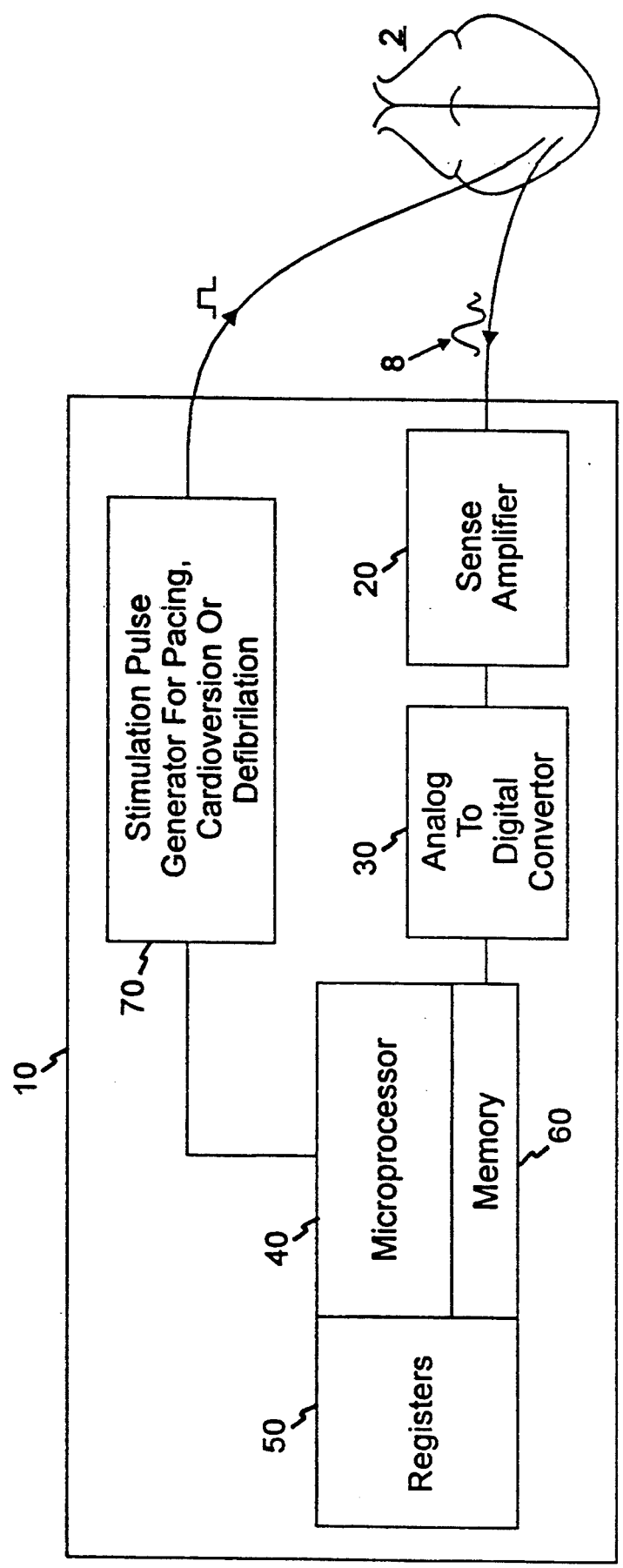
FIG. 3 is a block circuit schematic diagram of an apparatus in accordance with a preferred embodiment of the invention.

Referring to FIG. 3, the detection of ventricular complexes 8 and the measuring of the amplitude of these ventricular complexes are performed by conventional electronic means 10, e.g., digital microprocessor 40 controlled devices having sense amplifiers 20, analog to digital conversion circuits 30 and suitable memory 60 and registers 50 for data processing and manipulation. The present invention is preferably implemented under software control, and occurs following acquisition of the cardiac electric signals by a conventional sense amplifier, preferably after the acquired signals have been conditioned and converted to digital form in the usual manner. Accordingly, the parameters Smax, Smin, DecS, Tper and Tmax are programmable. Representative electronic circuits are those found in the series of pacemakers available from Ela Medical, Montrouge, France, offered under the CHORUS trademark. The method also could be performed using discrete circuitry, if desired.

Figure 4:
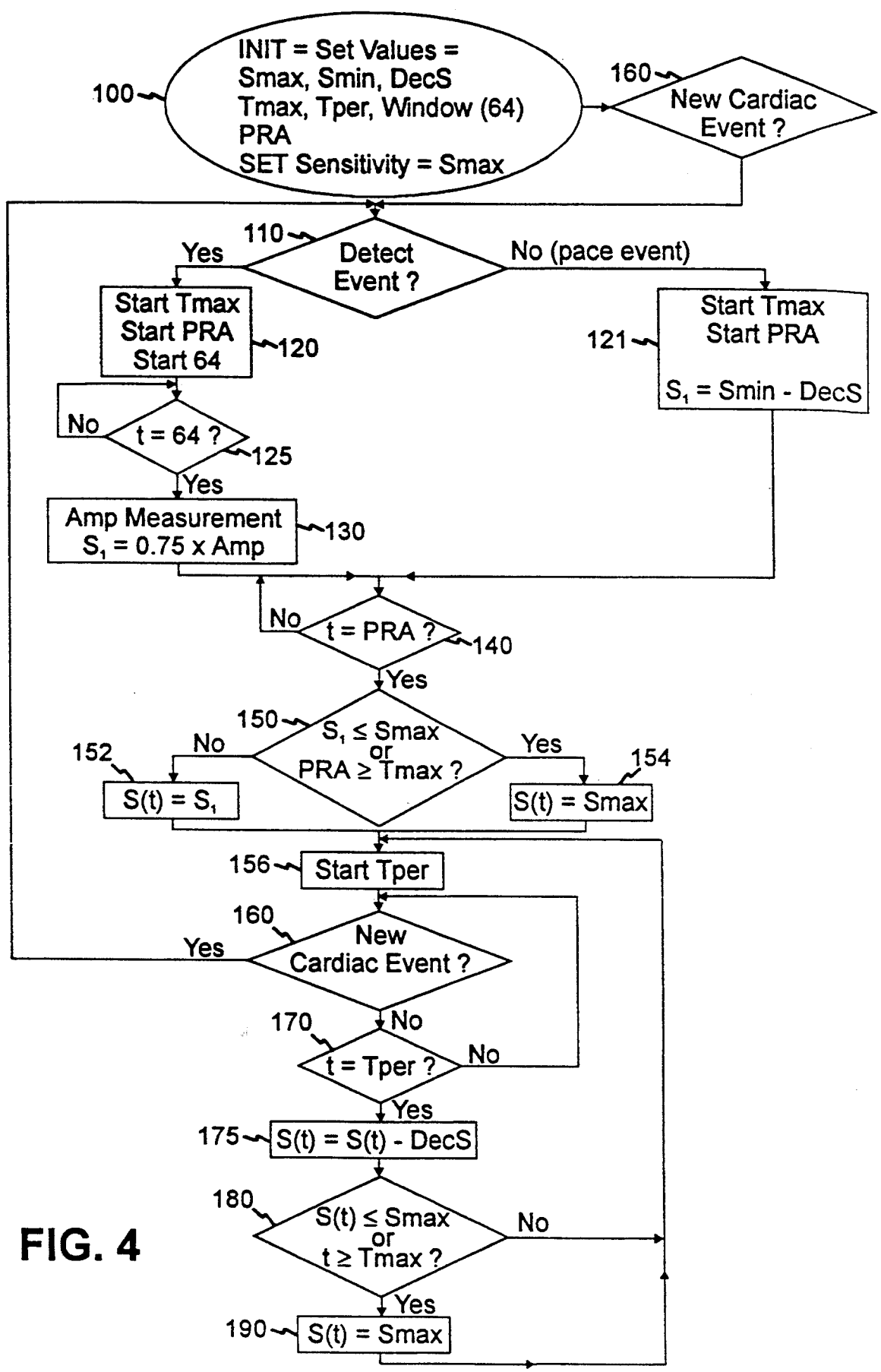
FIG. 4 is a flow chart for selecting and adjusting the sensitivity threshold in accordance with a preferred embodiment of the present invention.

For a software controlled cardiac control device, with reference to FIG. 4 one useful sequence of logic operations occurs as follows, on the basis of a time of detection t=0:
  (a) initializing of automatic sensitivity control (step 100);
  (b) during the absolute refractory period PRA:
    (1) measurement of the maximum amplitude Amp of the ventricular complex in the 64 ms window (step 130);
    (2) if PRA<Tmax: computation of the sensitivity threshold S1=Amp×75% to be implemented at the end of the absolute refractory period PRA (step 150), and
      (i) if S1>Smax, the computed value S1=Amp×75% is retained (step 152),
      (ii) otherwise, set S1=Smax (step 154);
    (3) If PRA≧Tmax, then S1=Smax (step 154);
  (c) from t=the end of the absolute refractory period PRA, e.g. t=110 ms, to t=Tmax, during each period Tper (steps 156–170):
    (1) the value of the sensitivity threshold S(t) computed during the previous period is used and maintained by conventional electronic means, e.g., a corresponding digital value;
    (2) computation of the sensitivity threshold value to be implemented at the end of the period Tper in process;
    (3) S(t+Tper)=S(t)−DecS (step 175), provided that (t+Tper) is below Tmax and that the computed sensitivity threshold value exceeds Smax (step 180). If one of these two conditions is not fulfilled, then S(t+Tper)=Smax (step 190).

In the case of a ventricular stimulation, the course of the logical operations is identical except for the initializing for which there is no amplitude measurement to be carried out. Instead, the initial sensitivity threshold applied at the end of the absolute refractory period is set at S1=Smin−DecS (step 121).

As noted, the cardiac monitoring device also may be a cardiac control device such as a pacemaker, cardioverter, or defibrillator, collectively illustrated in FIG. 3 as element 10 having a stimulation pulse generator 70 for delivering the appropriate stimulation pulse energy to the heart 2.

In the case of the cardiac pacemaker, the parameters can be programmed for a sensitivity setting aimed at enhancing the working of the pacemaker; oversensing is avoided and, with a short absolute refractory period PRA, the monitoring of the ventricular chamber is improved.

In the case of a defibrillator, the method for automatic sensitivity control enables detection of the fast R waves and possibly of the low-amplitude R waves corresponding to ventricular tachycardia, without detection of the T waves, thus enabling detection of ventricular tachycardia.

One skilled in the art will appreciate that the present invention can be practiced by other than the described embodiments, which are presented for purposes of illustration and not of limitation.

We claim:

1. A method for automatic control of sensitivity for a cardiac signal monitoring device, characterized by the following stages:
  (a) initially setting the sensitivity threshold (S) to a low value (Smax) so as to have maximum sensitivity; and thereafter
  (b) detecting a ventricular complex as the beginning of a cardiac cycle, measuring the amplitude (Amp) of the detected ventricular complex, and computing the sensitivity threshold (S) as a function of that sole measured amplitude (Amp);
  (c) subsequently decreasing the sensitivity threshold in stages during said same cardiac cycle until the sensitivity threshold (S) is at said low value; and
  (d) repeating stages (b) and (c) in response to each new cardiac cycle.

2. The method of claim 1 characterized in that the decreasing in stages of said sensitivity threshold further comprises decreasing the sensitivity by decrements (DecS).

3. The method of claim 2 characterized in that decreasing in stages further comprises providing a first time interval and a uniform decrement, lowering the sensitivity threshold by said uniform decrement following each occurrence of said first time interval during which no cardiac event is detected, and wherein measuring the amplitude in stage (b) further comprises rectifying the ventricular complex and measuring the maximum amplitude of the rectified ventricular complex, wherein said uniform decrement is on the order of 0.8 mV and said first time interval is on the order of 47 ms.

4. The method as claimed in claim 1 characterized by counting from the detection of a ventricular complex a selected maximum period (Tmax) and, at the end of the selected maximum period (Tmax), returning the sensitivity threshold (S) to the low value (Smax) corresponding to maximum sensitivity.

5. The method of claim 1 characterized by providing a time window and measuring the amplitude (Amp) of said detected ventricular complex during said time window, the time window being selected from between 16 and 110 ms counted from the detection of a ventricular complex.

6. The method of claim 5 wherein the selected time window is on the order of 64 ms.

7. The method of claim 1 wherein the cardiac signal monitoring device is a cardiac pacemaker.

8. The method of claim 1 wherein the cardiac signal monitoring device is one of a cardioversion device and a defibrillation device.

9. A cardiac control device selected from among the group consisting of pacemaker, a cardioversion device and a defibrillation device, characterized in that it comprises a ventricular complex detection sensitivity threshold that can be automatically adjusted by the method of claim 1.

10. A cardiac monitoring device for sensing cardiac electrical signals and detecting cardiac events characterized by:
    means for providing an initial sensitivity threshold having a low value corresponding to maximum sensitivity;
    means for providing a time window following a sensed cardiac event and a time interval;
    means for providing an absolute refractory period in response to a sensed cardiac event;
    means for detecting the maximum amplitude of the sensed cardiac electrical signals occurring during said time window following said sensed cardiac event;
    means for adjusting the sensitivity threshold to a value that is a function of the detected amplitude, said adjustment occurring at the end of the absolute refractory period; and
    means for subsequently decreasing the sensitivity threshold following each occurrence of said time interval in the absence of said detecting means detecting a subsequent cardiac event, said decreasing means not decreasing the sensitivity level below the provided low value.

11. The device of claim 10 wherein the adjusting means comprises means for adjusting the sensitivity threshold to be a percent of the maximum amplitude of the sensed cardiac signals detected during said time window.

12. The device of claim 11 wherein the percent is on the order of 75%.

13. The device of claim 10 wherein the cardiac monitoring device further comprises a pacemaker including a cardiac stimulation pulse generator.

14. The device of claim 13 wherein the adjusting means is further characterized by:
    means for providing a sensitivity threshold that is a high value corresponding to a minimum sensitivity; and
    second means for adjusting the sensitivity threshold in response to a cardiac stimulation pulse to be a value less than the high value.

15. The device of claim 14 wherein the selected value of the second adjusting means is the minimum sensitivity threshold less a selected amount, the selected amount corresponding to the amount by which the sensitivity threshold is decreased following each time interval.

16. The device of claim 10 further comprising means for providing a decrement and characterized in that the decreasing means decreases the sensitivity threshold by said decrement after the occurrence of each selected time interval.

17. The device of claim 16 wherein the detecting means further comprises rectifying the cardiac electrical signal, the selected decrement is on the order of 0.8 mV, the time interval is on the order of 47 ms, and the maximum amplitude of the cardiac electrical signal is the maximum of the rectified cardiac electrical signal.

18. The device of claim 10 characterized in that the adjusting means further comprises means for counting a maximum period (Tmax) from the detection of a cardiac event and means for returning the sensitivity threshold to the low value corresponding to maximum sensitivity at the end of the maximum period (Tmax).

19. The device of claim 10 characterized in that the time window is selected from between 16 and 110 ms counted from the detection of the cardiac event.

20. The device of claim 19 wherein the selected time window is on the order of 64 ms.

21. The device of claim 10 in which the cardiac monitoring device is selected from among the group consisting of a cardiac pacemaker, a cardioversion device, and a cardiac defibrillation device.

22. A method for controlling sensitivity to cardiac electrical signals characterized by:
    providing a circuit having a sensitivity threshold for sensing cardiac electrical signals corresponding to cardiac events;
    providing an absolute refractory period following each detected cardiac event;
    providing an initial sensitivity threshold having a low value corresponding to maximum sensitivity;
    detecting the occurrence of a cardiac event;
    detecting the maximum amplitude of the electrical signals corresponding to a sensed cardiac event occurring during a selected time window following said sensed cardiac event;
    adjusting the sensitivity threshold, at the end of the absolute refractory period, to a value that is a function of the detected maximum amplitude; and
    decreasing the sensitivity threshold following each occurrence of a selected time interval during which no cardiac event is sensed but not below the provided low value.

23. The method of claim 22 wherein adjusting the sensitivity threshold further comprises selecting a value that is a percent of the maximum amplitude of the sensed cardiac signals detected during the window.

24. The method of claim 23 wherein the percent is on the order of 75%.

25. The method of claim 22 further comprising providing a selected minimum sensitivity threshold, providing a pacemaker and a generator for outputting cardiac stimulation pulses, wherein the adjusting step is further characterized by adjusting the sensitivity threshold in response to a cardiac stimulation to be a threshold value that is less than the selected minimum sensitivity threshold value.

26. The method of claim 25 wherein decreasing the sensitivity threshold further comprises decreasing the threshold by a uniform decrement after each time interval and the selected value is the minimum sensitivity threshold value less said decrement.

27. The method of claim 22 characterized in that decreasing the sensitivity threshold is characterized by decreasing the sensitivity threshold by a decrement after the occurrence of each selected time interval.

28. The method of claim 27 wherein the selected decrement is on the order of 0.8 mV, the time interval is on the order of 47 ms, and the detecting step further comprises rectifying the cardiac electrical signals and detecting the maximum amplitude of the rectified cardiac electrical signal.

29. The method of claim 22 characterized in that the adjusting step further comprises providing a selected maximum period (Tmax), counting the maximum period (Tmax) from the detection of a cardiac event, and at the end of the maximum period (Tmax), setting the sensitivity threshold to the low value corresponding to maximum sensitivity.

30. The method of claim 22 characterized in that the detecting step is characterized by detecting the maximum amplitude during a time window selected from between 16 and 110 ms counted from the detection of the cardiac event.

31. The method of claim 30 wherein the selected time window is on the order of 64 ms.

32. The method of claim 22 wherein the circuit providing step further comprises providing said circuit to a cardiac control device selected from among the group consisting of a cardiac pacemaker, a cardioversion device, and a cardiac defibrillation device.

* * * * *

UNITED STATES PATENT AND TRADEMARK OFFICE
CERTIFICATE OF CORRECTION

PATENT NO. : 5,339,820
DATED : August 23, 1994
INVENTOR(S) : Henry et al.

It is certified that error appears in the above—identified patent and that said Letters Patent is hereby corrected as shown below:

Column 6, line 62, after "low value" insert --(Smax)--,

Signed and Sealed this

Eleventh Day of April, 1995

Attest:

BRUCE LEHMAN

Attesting Officer     Commissioner of Patents and Trademarks